US009511017B2

(12) United States Patent
Kritzler

(10) Patent No.: US 9,511,017 B2
(45) Date of Patent: Dec. 6, 2016

(54) METHOD AND COMPOSITION FOR USE IN PREPARATION OF A PATIENT FOR SURGERY

(75) Inventor: Steven Kritzler, Cronulla (AU)

(73) Assignee: Novapharm Research (Australia) Pty Ltd, Rosebery, New South Wales (AU)

( * ) Notice: Subject to any disclaimer, the term of this patent is extended or adjusted under 35 U.S.C. 154(b) by 1266 days.

(21) Appl. No.: 13/010,197

(22) Filed: Jan. 20, 2011

(65) Prior Publication Data

US 2011/0117048 A1 May 19, 2011

Related U.S. Application Data

(62) Division of application No. 11/914,539, filed as application No. PCT/AU2006/000553 on Apr. 28, 2006, now abandoned.

(30) Foreign Application Priority Data

May 16, 2005 (AU) .............................. 2005902493

(51) Int. Cl.
| | |
|---|---|
| *A01N 25/02* | (2006.01) |
| *A61K 9/00* | (2006.01) |
| *A61L 2/00* | (2006.01) |
| *A61K 47/10* | (2006.01) |
| *A61K 47/14* | (2006.01) |
| *A61K 47/16* | (2006.01) |
| *A61K 47/18* | (2006.01) |
| *A61K 47/20* | (2006.01) |
| *A61K 47/32* | (2006.01) |
| *A61K 47/38* | (2006.01) |

(52) U.S. Cl.
CPC ............ *A61K 9/0014* (2013.01); *A01N 25/02* (2013.01); *A61L 2/0088* (2013.01); *A61K 47/10* (2013.01); *A61K 47/14* (2013.01); *A61K 47/16* (2013.01); *A61K 47/18* (2013.01); *A61K 47/20* (2013.01); *A61K 47/32* (2013.01); *A61K 47/38* (2013.01)

(58) Field of Classification Search
CPC .. A01N 2300/00; A01N 25/04; A01N 59/16; A01N 25/30; A01N 25/10; A01N 25/34; A01N 31/02; A01N 65/00; A01N 59/20; A01N 25/12; A01N 25/16; A01N 25/08; A01N 59/00; A01N 43/40; A01N 25/28
See application file for complete search history.

(56) References Cited

U.S. PATENT DOCUMENTS

| | | | |
|---|---|---|---|
| 4,335,115 A | 6/1982 | Thompson et al. | |
| 4,975,271 A | 12/1990 | Dunn et al. | |
| 5,624,906 A * | 4/1997 | Vermeer ................. | A61K 8/60 514/23 |
| 5,656,286 A | 8/1997 | Miranda et al. | |
| 5,747,058 A | 5/1998 | Tipton et al. | |
| 6,299,900 B1 * | 10/2001 | Reed ...................... | A61K 8/046 424/448 |
| 6,951,642 B2 | 10/2005 | Scholz et al. | |
| 2002/0022660 A1 | 2/2002 | Jampani et al. | |
| 2003/0113356 A1 | 6/2003 | Deckner et al. | |
| 2004/0219227 A1 | 11/2004 | Modak et al. | |
| 2006/0052452 A1 * | 3/2006 | Scholz ................. | A61K 9/0014 514/557 |

FOREIGN PATENT DOCUMENTS

| | | |
|---|---|---|
| JP | 2003-515612 | 5/2003 |
| WO | WO 98/44930 | 10/1998 |
| WO | WO98/53036 | 11/1998 |
| WO | 00/15036 A1 | 3/2000 |
| WO | 01/41567 A1 | 6/2001 |
| WO | 01/41573 A1 | 6/2001 |
| WO | 03028766 A1 | 4/2003 |
| WO | 03/034994 A2 | 5/2003 |
| WO | WO2004/028502 | 4/2004 |
| ZA | 9907202 B | 5/2000 |

OTHER PUBLICATIONS

Nielsen et al. J. clin Path., 1975, 28, 793-797.*
Jorgensen et al. "Effect of a Chlorhexidine Dressing on the Healing after Periodontal Surgery", J. Periodontal, Jan. 1974, pp. 13-17.*
Jorgensen et al. ("Effect of a Chlorhexidine Dressing on the Healing after Periodontal Surgery", J. Periodontol., Jan. 1974, pp. 13-17).*
Supplemental European Search Report of EP 06 72 1433 dated Nov. 19, 2012.
Sebben et al., "Surgical antiseptics", Journal of the American Academy of Dermatology, C.V. Mosby, St. Louis, MO, US, vol. 9, No. 5 (Nov. 1, 1983) pp. 759-765.
D.J. Byrne, et al., "Rationalizing whole body disinfection," Journal of Hospital Infection, (1990), vol. 15, pp. 183-187.
R.A. Garibaldi, "Prevention of intraoperative wound contamination with chlorhexidine shower and scrub," Journal of Hospital Infection, (1988), vol. 11, (Supplement B), pp. 5-9.
Xue Guangbo et al., "[Modern] Antisepsis," People's Military Medical Press, Jul. 2002, pp. 444-463.
Kirschner et al., "Transdermal resorption of an ethanol and 2-propanol-containing skin disinfectant," Langenbecks Arch Surg., 2009, vol. 394, pp. 151-157.

(Continued)

*Primary Examiner* — Audrea Buckley
(74) *Attorney, Agent, or Firm* — Merchant & Gould P.C.

(57) ABSTRACT

Composition for application to skin comprising a biocide or combination of biocides (such as chlorhexidine, halogenated phenols, quaternary ammonium compounds; povidone-iodine; zinc pyridinethione; alcohols etc.) and at least one transcutaneous vehicle (for example alkyl methyl sulfoxides, alkyl pyrrolidones, glycols, glycol ethers and glycol esters) effective to convey the biocide to a sub epidermal "resident" micro-organism. Also a method for preparing a patient for surgery comprising the step of treating an area of the patient's skin at, and in the surrounding the vicinity of, the site of an intended surgical incision with a composition effective to kill more than 93% of both "transient" and "resident" micro-organisms.

18 Claims, No Drawings

(56) References Cited

OTHER PUBLICATIONS

Luo Jieying et al., "Theory and Practice of Modern Physical Pharmaceutics," first edition, Shanghai Science and Technology Literature Publishing House, Apr. 2005, pp. 288-340.
Nielsen, M.L. et al., "Anaerobic . . . chlorhexidine: . . . volunteers," Journal of Clinical Pathology, 1975, vol. 28, pp. 793-797.
Paulson, D.S., "Efficacy . . . shower wash," Am. Journal of Inf. Control, 1993, vol. 21, pp. 205-209.
Ritter, M.A. et al., "The antimicrobial . . . clinical study," J Bone Joint Surg. Am., 1980, vol. 62, pp. 826-828 (Abstract).
State Intellectual Property Office of P.R. of China, The Notification of the First Office Action, Chinese Application No. 200680016994.X, May 4, 2010.
International Search Report (PCT/AU2006/000553; mailed May 29, 2006).
Office Action from corresponding European Patent Application No. 06 721 433.8, mailed Aug. 24, 2016.
S. Pandey et al., "Development and evaluation of transdermal formulations containing metronidazole and norfloxacin for the treatment of burn wound", Indian Journal of Experimental Biology, vol. 37, May 1999, pp. 450-454.

\* cited by examiner

METHOD AND COMPOSITION FOR USE IN PREPARATION OF A PATIENT FOR SURGERY

CROSS REFERENCE TO RELATED APPLICATIONS

The present application is a divisional of U.S. patent application Ser. No. 11/914,539, filed Nov. 15, 2007, which is a national phase of International Application No. PCT/AU2006/000553, filed Apr. 28, 2006, which claims priority to Australian Patent Application No. 2005902493, filed May 16, 2005, each of which is herein incorporated by reference in its entirety.

FIELD OF THE INVENTION

The present invention is concerned with an improved method for preparing a patient for surgery. More particularly, the present invention is concerned with reducing the risk (in comparison with methods currently employed) of a patient contracting an infection as a result of undergoing a surgical procedure. The present invention is also concerned with compositions suitable for use in the method.

Although the method will be herein described with reference to preparation of human patients for surgery it will be understood that the method is equally applicable to other animals.

BACKGROUND OF THE INVENTION

It is usual when preparing a patient for surgery to treat an area surrounding the intended site of an incision by applying a biocide such as iodine or chlorhexidine to the skin surface. This is usually applied immediately preoperatively. After treatment, the area is covered with a sterile sheet or drape leaving an opening through which the surgeon can make an incision and perform an operation. The purpose of this procedure is to kill any colonies of micro-organism which exist on the patient's skin and which may access the surgical site giving rise to infection of the surgical wound. Although this procedure is largely effective in reducing the occurrence of post operative infection, a high proportion of cases in which infection does occur are attributed to autologous infection. Such infection if it does occur may have serious, or even fatal, consequences.

It is the practice in some hospitals as an added precaution to ask patients to wash themselves, or at least the areas intended for surgery, with an antiseptic soap once a day for one or two days prior to surgery. This wash is usually done under the shower and is thought to reduce the bacterial load on the patient's skin, and to remove micro-organisms from a wider area of skin than is practical in the operating theatre prior an operation.

The above treatments have in common that they are only effective against "transient" micro-organisms. "Transient" micro-organisms are those that exist on the surface of skin. The efficacy of such treatments against transient micro-organisms is discussed by Paulson, D. S. (American Journal of infection Control (1993), 21, 205-209) in respect of 4% chlorhexidine gluconate shower baths and Byrne, D. J. et al (J. Hospital Infection (1990), 15, 183-187) in respect of 4% chlorhexidine detergent. Garibaldi, R. A. (J. Hospital infection (1988), 11, Sup B 5-9) showed that 4% chlorhexidine gluconate was more effective than povidone iodine or triclocarban medicated soap for treating skin surface colonization. Nevertheless the frequency of intra-operative wound cultures was at best 4%, i.e. surface cultures were found on 4 patients in 100 intra-operatively.

Any discussion of the prior art throughout the specification should in no way be considered as an admission that such prior art is widely known or forms part of common general knowledge in the field.

The present inventor has observed that while a patient's skin is treated pre-operatively with a biocide effective against "transient" micro-organism populations, surgeons are obliged to "scrub up" and this "surgical scrubbing" involves intensive scrubbing treatment with biocides and surfactants extending over several minutes under running water according to complex set down protocols. These scrubbing protocols are intended not only to remove "transient" organisms from the surface of the surgeon's hands, but also to kill "resident" micro-organisms which may reside within pores of the skin. The epidermis which is the outer layer of skin consists of five stratum, of which the stratum corneum is the outermost. Some micro-organisms may reside sub corneum, particularly but not only in sweat glands, hair follicles, and subcutaneous glands. Such "resident" micro-organisms are difficult to kill even with scrubbing and studies have shown that their removal is only partially accomplished by surgical scrubbing. It would be impracticable to scrub patients under running water to the same extent prior to surgery and doing so would only be partially effective The commonly used preoperative compositions result in approximately a reduction of 2 log in "transient" micro-organisms on dry areas of skin, a reduction of 3 log on moist areas of skin (when measured in-vivo on hands and wrists using the "glove juice method" and when measured on fingertips using the "European method"), and have substantially no effect on the population of "resident" micro-organisms in the skin. The occurrence of "resident" micro-organisms varies greatly from one person to another and variations of up to ten fold in resident micro-organism counts can be found in a representative sample of a population. Since the normal preoperative treatment is relatively effective against "transient" micro-organisms, this implies that "resident" micro-organisms may play a role in autologous infection.

Neilsen et al. (J. Clinical Pat., (1975), 28, 793-797) examined the effect of 0.5% chlorhexidine in 62% ethyl alcohol on both superficial "transient" and "resident" flora. They concluded that a two step process including a pretreatment with a detergent was essential for treating "resident" flora. Of fourteen volunteers examined, sub-corneum aerobic micro-organisms were found in each prior to treatment and remained in at least one case subsequent to the preferred treatment—i.e. a failure rate of 7%. The authors could only conclude that the treatment must be said "to eliminate to a high degree" the patients skin as a source of anaerobic and aerobic operation wound bacteria. Regretfully the intervening 30 years have shown even that conclusion to be unrealistically optimistic and the problem remains.

PCT/US98/06779 describes a method for preoperative skin preparation involving iodine and ethyl alcohol in a gel. Although the specification notes that micro-organisms may be "transient' or "resident', it contains no data or claim as to efficacy in respect of "resident" micro-organisms. Although primarily directed to an iodine based composition, the method disclosed (page 26) involves application of the gel to the surgical site immediately preoperatively with scrubbing for about 30 seconds. Both the composition and method differ from that herein disclosed.

It is also critically important to note that in the cited examples the primary biocides are chlorhexidine or iodine and with those biocides little, if any, subcutaneous penetration is possible because of the strong interactions between these biocidal actives and all body proteins. In the case of chlorhexidine these interactions cause the biocide to become attached (substantive) to the protein and in the case of iodine cause it to be deactivated by the protein. Therefore any subcutaneous action is dependant upon the ethanol contained therein.

This penetrating ethanol is quickly dissipated within the body and therefore there is no residual biocidal activity sub corneum beyond a few minutes. Recolonisation of these areas begins immediately after alcohol dissipation. Most surgical procedures take between 15 minutes and six hours.

Because of the currently perceived risk of post operative infection (including autologous infection) surgeons today routinely prescribe preoperative antibiotics as a prophylactic measure. This practice risks increasing the resistance of micro-organisms to antibiotics and is a major medical and social concern.

It is an object of the present invention to overcome or ameliorate at least one of the disadvantages of the prior art. It is an object of preferred embodiments of the invention to provide improved methods of preparing a patient for surgery and compositions for use in that method which in highly preferred embodiments are more effective at reducing post operative infection than one or more prior art methods.

BRIEF STATEMENT OF INVENTION

The present inventor has found that a preparation including one or more biocides and a transcutaneous vehicle effective to carry the biocide as a solution across the dermal barrier is effective to kill the "resident" micro-organisms especially when applied repeatedly several times a day over several days preceding an operation. Desirably the composition is applied as a gel or cream and spread over a relevant area of skin. The composition may be self applied by the patient on instruction by the surgeon and will usually be left in place until a subsequent application.

According to a first aspect the invention provides a composition for application to skin comprising at least one biocide and at least one transcutaneous vehicle effective to convey the biocide to "resident" micro-organisms. For preference, the transcutaneous vehicle is selected from the group consisting of suitable alkyl sulfoxides, alkyl pyrrolidones, glycols, glycol ethers and glycol esters.

The "resident" micro-organisms may be sub epidermal.

"Transcutaneous" in respect of the vehicle means that the vehicle penetrates at least to the subcutis and desirable through the subcutis. Skin is the largest human organ and consists of three functional layers: epidermis, dermis, and subcutis. Skin is designed to protect the organism from water loss and mechanical, chemical, microbial, and physical penetration and is specially structured to achieve these tasks. Those skilled in the art will recognise that while ethanol and similar alkyl alcohols have some ability to penetrate into the corneum, they are not transcutaneous and do not penetrate to the subcutis. Transcutaneous vehicles have been developed for transporting systemic drugs across the skin barrier, but have not previously been used to transport biocides into skin.

Combinations of biocides are preferred for use in the invention and an especially preferred combination is triclosan with phenoxyethanol. Care needs to be taken that in the concentrations used the biocides have no adverse systemic effect According to a second aspect the invention provides a method for preparing a patient for surgery comprising the step of treating an area of the patient's skin at, and in the surrounding the vicinity of, the site of an intended surgical incision with a composition effective to kill more than 93% of both "transient" and "resident" micro-organisms. Preferred embodiments employ a composition according to the first aspect and leave virtually no surviving "resident" or "transient" micro-organisms.

The term "comprising" is herein used in an inclusive sense that is to say in the sense of "including" or "containing". The term is not intended in an exclusive sense ("consisting of" or "composed or").

In preferred embodiments the composition contains at least one, and preferably a combination of biocides and these are formulated so as to be able to access subcutaneous "resident" micro-organisms. In preferred embodiments of the invention the method is used in conjunction with prior art methods of preparation including showering with antibacterial soap and skin prepping on the operating table. It is not intended that the method be used as a substitute for skin prepping.

According to a third aspect the invention provides a method according to the first aspect, wherein said step is repeated at least once, during the 24 hours preceding an operation.

In preferred embodiments of the method of the invention, a procedure according to the second aspect is repeated at least once a day for several days prior to the operation.

Suitable biocides for use in compositions according to the invention include, without limitation, chlorhexidine and its salts; dichlorophene, other chlorophenol derivatives such as p-chloro-m-xylenol, chlorophene and o-phenylphenol, 2,4,4-trichloro-2-hydroxy-diphenylether (triclosan); octenidin-dihydrochloride $(CH_3-(CH_2)_7-NHON-(CH_2)_{10}-NO-NH(CH_2)_7-CH_2$ or any other salt thereof, quaternary ammonium compounds, povidone-iodine, and zinc pyridinethione, and phenoxy ethanol Suitable salts of chlorhexidine include the gluconate, isethionate, formate, acetate, glutamate, succinamate, mono-diglycolate, dimethanesulfonate, lactate, diisobutyrate or the glucoheptonate salts.

Other suitable biocides include selected alcohols such as ethyl, methyl, isopropyl and phenyl alcohol.

Preferably the antimicrobial agent has a water solubility of at least 0.001% w/v at ambient temperature.

When the antimicrobial agent is chlorhexidine digluconate it is used in an amount preferably not exceeding 4.5% w/v. When the antimicrobial agent is 2,4,4-trichloro-2-hydroxydiphenylether (triclosan) it is used in an amount preferably not exceeding 3% w/v. Preferably two or more biocides are used in combination. Biocides such as iodine compounds and chlorhexidine compounds react with protein and are not suitable for dermal penetration since they would be deactivated by skin protein, but are effective against "transient" micro-organisms. Combinations of triclosan with phenoxy ethanol have been found to be unexpectedly effective for use in the invention and exhibit a desirable synergy.

Compositions according to the invention may be formulated into a liquid, lotion, cream, gel, or other topical vehicle, or may be formulated as a spray. The composition can be aqueous or alcoholic utilising ethanol, n-propanol or isopropanol.

In addition to one or more biocides, the formulation includes at least one vehicle in which a biocide is soluble and which is effective to transport the biocide transdermally. The vehicle is selected from the group consisting of suitable alkyl sulfoxides, alkyl pyrrolidones, glycols, glycol ethers and suitable esters. Examples of such vehicles include, without limitation, dimethyl sulfoxide as an example of a suitable alkyl sulfoxide; N-methyl-2-pyrrolidone as an example of a suitable alkyl pyrrolidone; propylene glycol as an example of a suitable glycol, isopropylmyristate as an example of a suitable ester and diethylene glycol monoethyl ether as an example of a suitable glycol ether. The use of sulfoxides may require medical prescription in some jurisdictions.

PREFERRED EMBODIMENTS OF THE INVENTION

Preferred embodiments of the invention will now be described by way of example only.

Example 1

A Gel Suitable for Use in a Method According to the Invention

| | |
|---|---|
| Ethanol | 70.00% w/w |
| Water | 10.39% |
| Hydroxypropyl cellulose | 0.60% |
| Phenoxy ethanol | 2.00% |
| Triclosan | 1.00% |
| Dimethylsulfoxide | 10.00% |
| Propylene Glycol | 5.00% |
| Isopropylmyristate | 1.00% |
| Dyestuff | 0.01% |

In example 1 the ethanol serves as a biocide for transient organisms, as a skin penetrant, a solvent, and as a drying aid. Water acts as a solvent, and activator of ethanol as biocide. Hydroxypropyl cellulose acts as a gelling agent. Phenoxy ethanol acts as a preservative and as a secondary biocide for transient and subcutaneous micro-organisms. Triclosan acts as the primary biocide for killing transient and subcutaneous micro-organisms. Dimethylsulfoxide is the transcutaneous vehicle. Propylene Glycol also acts as a transcutaneous vehicle. Isopropylmyristate also acts as a transcutaneous vehicle and skin emollient. Dyestuff is added as an indicator that the required area of skin has been appropriately treated.

An example of a suitable method according to the invention involves a patient being instructed by the patient's surgeon to spread the gel of Example 1 over an area of the skin covering at least a margin of about 5 cm around the site of intended incision in all directions at a rate of from about 0.03 to 0.1 g/sq. cm. of skin surface. The gel should be rubbed into the skin twice per day at 8 hr intervals for three days prior to the date of the operation and once applied should be left in place and desirably should not be washed off.

Example 2

An embodiment of a cream according to the invention and suitable for use in a method according to the invention has the following composition. The main function of each component is indicated in the table.

| Commercial name | Chemical name | Contents (% w/w) | Function |
|---|---|---|---|
| BPO | Benzoyl peroxide | 5.00% | Actives |
| Irgasan DP300 | Triclosan | 1.00% | Actives |
| Pharmasolv | N-Methyl pyrrolidone | 10.00% | Transdermal enhancer |
| EDTA 2Na | Disodium Ethylene Diamine Tetra Acetic Acid | 3.00% | Chelating agent, stabiliser |
| Glycerol | Glycerol | 2.00% | Moisturiser |
| Carbopol 940 | Carbomer(Acrylic copolymer) | 0.90% | Viscosity modifier |
| Pentane - DB | Benzyl benzoate | 3.00% | Skin emollient |
| DPG | Dipropylene glycol | 3.00% | Moisturiser |
| Crodasinic LS30 | Sodium Lauroyl Sarcosinate(30%) | 2.00% | Emulsifier |
| Promulgen - G | Stearyl alcohol (and) Polyethyleneglycol 1000 cetyl/stearyl ether | 2.00% | Emollient/ emulsifier |
| PVP K-15 | Polyvinylpyrrolidone | 0.10% | Skin feel enhancer |
| Phenoxyethanol | Phenoxyethanol | 2.00% | Active - secondary biocide |
| TEA 99% | Triethanolamine | 0.19% | pH modifier |
| Ethanol 100% | Ethyl alcohol | 10.00% | Solvent/ formulation aid |
| P-water | Water | 55.80% | Solvent |
| | Dyestuff | 0.01% | Treatment marker |
| | TOTAL | 100.00% | |

In use a patient is instructed by the patient's surgeon to spread the cream of Example 2 over an area of the skin covering at least a margin of about 5 cm around the site of intended incision in all directions at a rate of from about 0.03 to 0.1 g/sq. cm. of skin surface. The cream should be rubbed into the skin at least twice per day (preferably at 8 hr intervals) for three days prior to the date of the operation and, once applied, should be left in place.

Example 3

A second embodiment of a cream according to the invention and suitable for use in a method according to the invention has the following composition. The main function of each component is indicated.

| Commercial name | Chemical name | Contents (% w/w) | Function |
|---|---|---|---|
| BPO | Benzoyl peroxide | 5.00% | Actives |
| Irgasan DP300 | Triclosan | 1.00% | Actives |
| Trancutol P | Diethylene Glycol Monoethyl Ether | 10.00% | Transdermal enhancer |
| EDTA 2Na | Disodium Ethylene Diamine Tetra Acetic Acid | 3.00% | Chelating agent, stabiliser |
| Glycerol | Glycerol | 2.00% | Moisturiser |
| Carbopol 940 | Carbomer(Acrylic copolymer) | 0.90% | Viscosity modifier |
| Pentane - DB | Benzyl benzoate | 3.00% | Skin emollient |
| DPG | Dipropylene glycol | 3.00% | Moisturiser |
| Crodasinic LS30 | Sodium Lauroyl Sarcosinate(30%) | 2.00% | Emulsifier |
| Promulgen - G | Stearyl alcohol (and) Polyethyleneglycol 1000 cetyl/stearyl ether | 2.00% | Emollient/ emulsifier |
| PVP K-15 | Polyvinylpyrrolidone | 0.10% | Skin feel enhancer |

-continued

| Commercial name | Chemical name | Contents (% w/w) | Function |
|---|---|---|---|
| Phenoxyethanol | Phenoxyethanol | 2.00% | Active - secondary biocide |
| TEA 99% | Triethanolamine | 0.19% | pH modifier |
| Ethanol 100% | Ethyl alcohol | 10.00% | Solvent/formulation aid |
| P-water | Water | 55.80% | Solvent |
|  | Dyestuff | 0.01% | Treatment marker |
|  | TOTAL | 100.00% |  |

The cream of example 3 is applied in a similar manner as described above with reference to example 1 or 2.

Example 4

A third embodiment of a cream according to the invention and suitable for use in a method according to the invention has the following composition. The main function of each component is indicated in the following table.

| Commercial name | Chemical name | Contents (% w/w) | Function |
|---|---|---|---|
| BPO | Benzoyl peroxide | 5.00% | Actives |
| Irgasan DP300 | Triclosan | 1.00% | Actives |
| Pharmasolv | N-Methyl pyrrolidone | 5.00% | Transdermal enhancer |
| Trancutol P | Diethylene Glycol Monoethyl Ether | 5.00% | Transdermal enhancer |
| EDTA 2Na | Disodium Ethylene Diamine Tetra Acetic Acid | 3.00% | Chelating agent, stabiliser |
| Glycerol | Glycerol | 2.00% | Moisturiser |
| Carbopol 940 | Carbomer(Acrylic copolymer) | 0.90% | Viscosity modifier |
| Pentane - DB | Benzyl benzoate | 3.00% | Skin emollient |
| DPG | Dipropylene glycol | 3.00% | Moisturiser |
| Crodasinic LS30 | Sodium Lauroyl Sarcosinate(30%) | 2.00% | Emulsifier |
| Promulgen - G | Stearyl alcohol (and) Polyethyleneglycol 1000 cetyl/stearyl ether | 2.00% | Emollient/emulsifier |
| PVP K-15 | Polyvinylpyrrolidone | 0.10% | Skin feel enhancer |
| Phenoxyethanol | Phenoxyethanol | 2.00% | Active - secondary biocide |
| TEA 99% | Triethanol amine | 0.19% | pH modifier |
| Ethanol 100% | Ethyl alcohol | 10.00% | Solvent/formulation aid |
| P-water | Water | 55.80% | Solvent |
|  | Dyestuff | 0.01% | Treatment marker |
|  | TOTAL | 100.00% |  |

The cream of example 4 is applied in a similar manner as described above with reference to examples 1, 2 or 3.

In each of the previous examples it is preferable for the patient in addition to the treatments described to shower or conduct a whole body wash using a disinfecting soap on the day of, and prior to, the operation Example 5

Relative Efficacy

The transcutaneous penetration and comparative release of active ingredient were compared using a horizontal glass Franz-type diffusion cells such as are described in R. Danids, (Skin Care Forum, Issue 37, August 2004, Cognis); S. Jung, (The University of California Irvine Undergraduate Research Journal, p. 25-26, Vol V, 2002, University of California Irvine); Guideline for Industry Non-sterile Semi-solid Dosage Forms (SUPAC-SS CMC7), May 1997, U.S. Department of Health and Human Services FDA CDER. A standard cellophane dialysis membrane of MW cut off 6-8000 was used for the diffusion studies. The Franz cell receiving solution was composed of 50% v/v methanol/water. Cellophane membranes were mounted horizontally in the Franz cells. 0.5 g of sample were used for each test. The cell receptor was continuously stirred magnetically and maintained at 35+/−2° C. At the designated time 150 microliters aliquots were sampled from the receiving vessel of the Franz cells. 20 microliters were injected into HLPC. The residue was returned to the Franz-cell and the cells topped up with additional receiving solution.

0.5 g samples of compositions according to examples 2, 3 and 4 were compared over periods of 2, 4 and 7 hours with a prior art composition comprising 5% chlorhexidine in 62% ethyl alcohol. The active ingredient was increased from 0.5% to 5% for the purposes of comparison with examples 2-4. Each test was in duplicate. HLPC analysis was performed using a C18 column, mobile phase 75% methanol, flow rate 1.5 mL/min. detector—UV 270 nm. The mean result of duplicate tests is tabulated below. Column A shows the composition example number, column B shows the time in hours. Column C, D, and E give the results for the actives in the respective formulations, both in mg and as a % of the sample quantity tested.

| A Example no. | B time (hrs) | C phenoxyethanol | | D triclosan | | E chlorhexidine | |
|---|---|---|---|---|---|---|---|
| | | mg | % | mg | % | mg | % |
| 2 | 2 | 0.6865 | 13.73 | 0.0119 | 0.24 | | |
|   | 4 | 1.0745 | 21.49 | 0.0246 | 0.49 | | |
|   | 7 | 1.4970 | 29.94 | 0.038 | 0.76 | | |
| 3 | 2 | 0.6495 | 12.99 | 0.0103 | 0.21 | | |
|   | 4 | 1.0150 | 20.3 | 0.0201 | 0.40 | | |
|   | 7 | 1.4080 | 28.16 | 0.0331 | 0.66 | | |
| 4 | 2 | 0.3355 | 6.71 | 0.0131 | 0.26 | | |
|   | 4 | 0.9960 | 19.92 | 0.0241 | 0.48 | | |
|   | 7 | 1.3645 | 27.29 | 0.0388 | 0.78 | | |
| 5 | 2 | | | | | 0.0026 | 0.052 |
|   | 4 | | | | | 0.0027 | 0.054 |
|   | 7 | | | | | 0.0039 | 0.078 |

It can be seen that phenoxy ethanol penetrates at a very much faster rate than either of the other biocides and to a much greater extent. After 2 hours more than 13% has penetrated compared with 0.24% of triclosan and even less of chlorhexidine. The difference is more substantial after 7 hrs. The penetration of biocides was much greater than for the prior art.

Example 6

Synergism Between Triclosan and Phenoxy Ethanol

An aqueous handwash formulation was prepared with three differing actives. Formula 1 contained triclosan 1% alone, formula 2 phenoxyethanol 2% alone, formula 3 triclosan 1% in combination with phenoxyethanol 2%. The three formulations were tested against an inoculum of

*Pseudomonas aeruginosa* against which triclosan alone is known to be relatively ineffective. The results were as follows:

| Formulation | Active ingredients | Initial conc. ATTC 15442 | Reduction at 30 secs contact | Reduction at 60 secs contact |
|---|---|---|---|---|
| formula 1 | Triclosan 1% | 1.2 × log 7 | 9.2 × log 2 | 3.0 log 3 |
| formula 2 | Phenoxyethanol 2% | 6.8 × log 6 | 1.2 log 2 | 3.0 log 3 |
| formula 3 | Triclosan 1% & Phenoxyethanol 2% | | 1.2 log 7 (total kill) | 1.2 log 7 (total kill) |

This data demonstrates a synergistic interaction between triclosan and phenoxy ethanol. This is particularly advantageous in the present case since the data in example 5 shows that phenoxyethanol penetrates at about 40 times the rate that triclosan alone or chlorhexidine alone would penetrate. In view of this data it is predictable that no subdermal micro-organisms would survive treatment over 2 hours, although repetitive treatment and treatment over longer periods would clearly be preferable.

Example 7

Cream Employing CHG/Phenoxyethanol as Actives

In this case the CHG is effective only against transient micro-organisms and the cream relies upon phenoxyethanol against resident micro-organisms.

| Commercial name | Chemical name | Contents (% w/w) | Function |
|---|---|---|---|
| | CHG | 1.00% | Actives |
| Pharmasolv | N-Methyl pyrrolidone | 10.00% | Transdermal enhancer |
| EDTA 2Na | Disodium Ethylene Diamine Tetra Acetic Acid | 3.00% | Chelating agent, stabiliser |
| Glycerol | Glycerol | 2.00% | Moisturiser |
| Carbopol 940 | Carbomer(Acrylic copolymer) | 0.90% | Viscosity modifier |
| Pentane - DB | Benzyl benzoate | 3.00% | Skin emollient |
| DPG | Dipropylene glycol | 3.00% | Moisturiser |
| Crodasinic LS30 | Sodium Lauroyl Sarcosinate(30%) | 2.00% | Emulsifier |
| Promulgen - G | Stearyl alcohol (and) Polyethyleneglycol 1000 cetyl/stearyl ether | 2.00% | Emollient/ emulsifier |
| PVP K-15 | Polyvinylpyrrolidone | 0.10% | Skin feel enhancer |
| Phenoxyethanol | Phenoxyethanol | 2.00% | Active - secondary biocide |
| TEA 99% | Triethanol amine | 0.19% | pH modifier |
| Ethanol 100% | Ethyl alcohol | 10.00% | Solvent/ formulation aid |
| P-water | Water | 55.80% | Solvent |
| | Dyestuff | 0.01% | Treatment marker |
| | TOTAL | 100.00% | |

Example 8

Cream Employing Povidone Iodine/Phenoxyethanol as Actives

| Commercial name | Chemical name | Contents (% w/w) | Function |
|---|---|---|---|
| | Povidone-iodine | 6.00% | Actives |
| Pharmasolv | N-Methyl pyrrolidone | 10.00% | Transdermal enhancer |
| EDTA 2Na | Disodium Ethylene Diamine Tetra Acetic Acid | 3.00% | Chelating agent, stabiliser |
| Glycerol | Glycerol | 2.00% | Moisturiser |
| Carbopol 940 | Carbomer(Acrylic copolymer) | 0.90% | Viscosity modifier |
| Pentane - DB | Benzyl benzoate | 3.00% | Skin emollient |
| DPG | Dipropylene glycol | 3.00% | Moisturiser |
| Crodasinic LS30 | Sodium Lauroyl Sarcosinate(30%) | 2.00% | Emulsifier |
| Promulgen - G | Stearyl alcohol (and) Polyethyleneglycol 100 cetyl/stearyl ether | 2.00% | Emollient/ emulsifier |
| PVP K-15 | Polyvinylpyrrolidone | 0.10% | Skin feel enhancer |
| Phenoxyethanol | Phenoxyethanol | 2.00% | Active - secondary biocide |
| TEA 99% | Triethanol amine | 0.19% | pH modifier |
| Ethanol 100% | Ethyl alcohol | 10.00% | Solvent/ formulation aid |
| P-water | Water | 50.81% | Solvent |
| | TOTAL | 100.00% | |

In this case the povidone iodine is effective only against transient micro-organisms and the cream relies upon phenoxyethanol against resident micro-organisms. The combination of triclosan with phenoxyethanol is preferred because the triclosan is persistently effective against transient micro-organisms (high residual activity) and also is persistent when transported sub cutaneously where it acts synergistically with the phenoxyethanol against resident micro-organisms.

The amount of gel applied will of course vary according to the formulation and the total area to be treated. Likewise, the frequency of application and the number of days prior the operation on which it should be applied as well as the exact area of application will vary with the formulation, skin type etc. and will need to be determined for each formulation in accordance with the invention by the surgeon in accordance with "best practice" guidelines. The determination of such protocols is a matter of routine testing upon large samples of patients.

Although developed for the preparation of patients for surgery with the intention of preventing or reducing the incidence of post operative infection, it will be apparent to those skilled in the art from the teaching hereof that compositions according to the invention have application for treating acne and other sub dermal or sub cutaneous infections.

Although the method is herein described with reference to preparation of human patients for surgery it will be understood that the method is equally applicable to other animals. It will also be apparent to those skilled in the art from the teaching hereof that the invention may be performed in other ways and using different formulations without departing from the inventive concept herein disclosed.

The claims defining the invention are as follows:

1. A method for preparing a patient for surgery, the method comprising the step of
applying a composition to a skin of the patient at a site of an intended surgical incision, said composition consisting essentially of:
a phenoxyethanol biocide in an amount effective against resident micro-organisms in the skin;
at least one additional biocide, in an amount effective against transient micro-organisms in the skin, selected from the group consisting of: chlorhexidine and salts thereof, a halogenated phenol and salts thereof, a quaternary ammonium compound, o-phenylphenol, povidone-iodine, polyvinylpyrrolidone-iodine complex, zinc pyridinethione, and an alcohol; and
at least one transcutaneous vehicle effective to convey the phenoxyethanol biocide across the skin's dermal barrier to a resident micro-organism.

2. A method according to claim 1 wherein the biocide of said composition comprises at least 2% of phenoxyethanol.

3. A method according to claim 1 wherein said step is repeated at least once in 24 hours immediately preceding an operation.

4. A method according to claim 1 wherein the step is repeated at least once a day for more than one day prior to an operation.

5. A method according to claim 1 wherein the step is repeated at least once a day for more than three days prior to an operation.

6. A method according to claim 1 wherein said step is repeated at least twice in 24 hours immediately preceding an operation.

7. A method according to claim 1 wherein said step is repeated at least four times in 48 hours immediately preceding an operation.

8. A method according to claim 1 wherein said step is repeated at least 6 times, during 72 hours immediately preceding an operation.

9. A method according to claim 1 conducted in combination with washing or showering using a biocidal soap or detergent, or a polyvinylpyrrolidone-iodine complex or a chlorhexidine presurgical prep.

10. A method according to claim 1 wherein the chlorhexidine salts are selected from the group consisting of: gluconate, isethionate, formate, acetate, glutamate, succinamate, monodiglycolate, dimethanesulfonate, lactate, diisobutyrate and glucoheptonate salt.

11. A method according to claim 1 wherein the alcohol is selected from the group consisting of ethyl, methyl, isopropyl and phenyl alcohol.

12. A method according to claim 1, wherein the chlorhexidine is chlorhexidine digluconate not exceeding 4.5% w/v.

13. A method according to claim 1, wherein the halogenated phenol is 2,4,4-trichloro-2-hydroxydiphenylether (triclosan) not exceeding 3% w/v.

14. A method according to claim 1, wherein the composition consists essentially of the phenoxyethanol biocide, the at least one additional biocide, and the at least one transcutaneous vehicle, wherein the at least one additional biocide is the halogenated phenol, and wherein the halogenated phenol is triclosan.

15. A method according to claim 1, wherein the at least one transcutaneous vehicle is selected from the group consisting of alkyl sulfoxides, alkyl pyrrolidones, glycols, glycol ethers and glycol esters.

16. A method according to claim 1, wherein the transcutaneous vehicle is one or more of polypropylene, diethylene glycol monoethyl ether, N-methylpyrrolidone, and isopropylmyristate.

17. A method according to claim 1, wherein the composition is formulated into a liquid, lotion, cream, gel, or other topical vehicle, or a spray.

18. A method according to claim 1, wherein the at least one transcutaneous vehicle effective to convey the phenoxyethanol biocide across the skin's dermal barrier to a resident micro-organism is present at a concentration of greater than 5% wt.

* * * * *